(12) United States Patent
Arrizza et al.

(10) Patent No.: US 11,185,240 B2
(45) Date of Patent: Nov. 30, 2021

(54) DEVICE FOR THE DIRECT DETECTION OF THE ENDOVASCULAR PRESSURE OF A FLUID IN A VESSEL

(71) Applicant: M.E.A. Pharma Sagl, Paradiso (CH)

(72) Inventors: Fabio Nicola Arrizza, Pescara (IT); Nicola Quinto, Arsago Seprio (IT); Stefano Costantini, Cassano Magnago (IT)

(73) Assignee: M.E.A. PHARMA SAGL, Paradiso (CH)

( * ) Notice: Subject to any disclaimer, the term of this patent is extended or adjusted under 35 U.S.C. 154(b) by 682 days.

(21) Appl. No.: 16/076,195

(22) PCT Filed: Feb. 6, 2017

(86) PCT No.: PCT/IB2017/050871
§ 371 (c)(1),
(2) Date: Aug. 7, 2018

(87) PCT Pub. No.: WO2017/141183
PCT Pub. Date: Aug. 24, 2017

(65) Prior Publication Data
US 2021/0177276 A1 Jun. 17, 2021

(30) Foreign Application Priority Data
Feb. 16, 2016 (IT) .................. 102016000015623

(51) Int. Cl.
*A61B 5/0215* (2006.01)
*A61M 1/16* (2006.01)
(Continued)

(52) U.S. Cl.
CPC ............. *A61B 5/0215* (2013.01); *A61M 1/16* (2013.01); *A61M 25/0014* (2013.01);
(Continued)

(58) Field of Classification Search
CPC ......... A61B 5/0215; A61B 2562/0347; A61M 1/16; A61M 5/34; A61M 39/02; A61M 25/0014
See application file for complete search history.

(56) References Cited

U.S. PATENT DOCUMENTS

| 3,786,810 A | 1/1974 | Pannier et al. |
| 3,807,389 A | 4/1974 | Kanbar et al. |

(Continued)

FOREIGN PATENT DOCUMENTS

| EP | 2301610 A2 | 3/2011 |
| GB | 2488810 A | 9/2012 |
| WO | 2014054791 A1 | 4/2014 |

*Primary Examiner* — Sean P Dougherty
*Assistant Examiner* — Alexander H Connor
(74) *Attorney, Agent, or Firm* — Volpe Koenig

(57) ABSTRACT

A device for the detection of endovascular pressure of a fluid in a vessel detects through an air column which inside capillary ducts, is in contact with endovascular fluid which exerts its pressure thereon, by separating such air column from outside in each process phase, and then prevents that the fluid from being polluted or infected thereby, and including a connector with a valve, which defines a connection terminal cavity arranged outside a needle-holding element and is in fluid communication with the capillary ducts through a duct extending from the needle-holding element to the connector; and a re-usable element including a pressure sensor and connector to connect to the connector at the terminal cavity of the disposable portion, which receives the pressure sensor, with the terminal cavity, the opening of the valve being determined by the connection between the re-usable element and the disposable portion.

11 Claims, 5 Drawing Sheets

(51) Int. Cl.
*A61M 25/00* (2006.01)
*A61M 39/02* (2006.01)
*A61M 5/34* (2006.01)

(52) U.S. Cl.
CPC ........ *A61B 2562/0247* (2013.01); *A61M 5/34* (2013.01); *A61M 39/02* (2013.01)

(56) References Cited

U.S. PATENT DOCUMENTS

| | | | |
|---|---|---|---|
| 5,454,374 | A | 10/1995 | Omachi |
| 5,954,701 | A | 9/1999 | Matalon |
| 7,927,270 | B2 | 4/2011 | Dlugos et al. |
| 2010/0094143 | A1 | 4/2010 | Mahapatra et al. |
| 2012/0031515 | A1* | 2/2012 | Whitaker ............... A61M 39/10 137/798 |
| 2013/0199722 | A1* | 8/2013 | Burbank ................ A61M 5/365 156/294 |
| 2014/0163516 | A1* | 6/2014 | Lareau .................... A61B 5/318 604/503 |

* cited by examiner

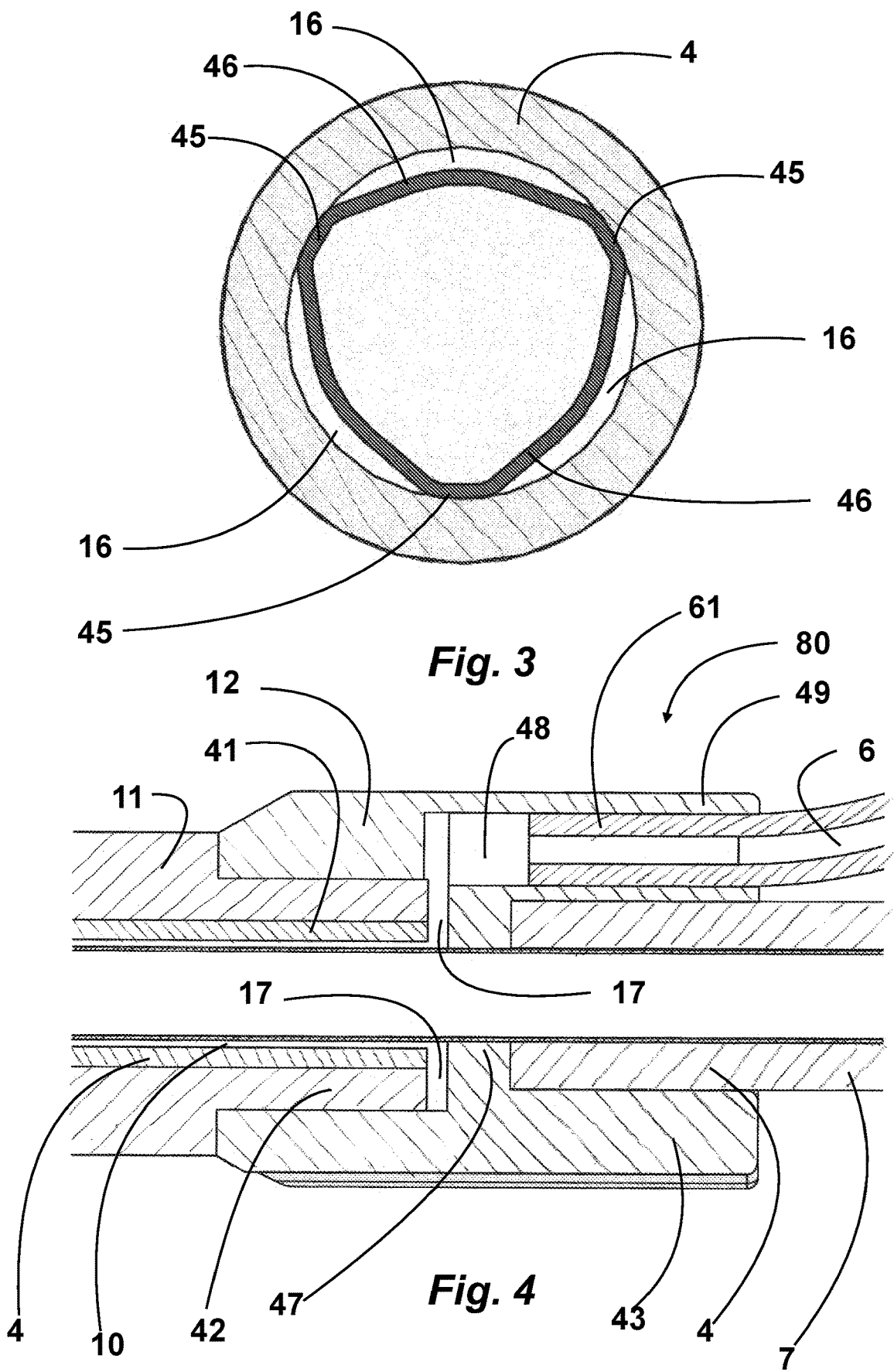

Fig. 9
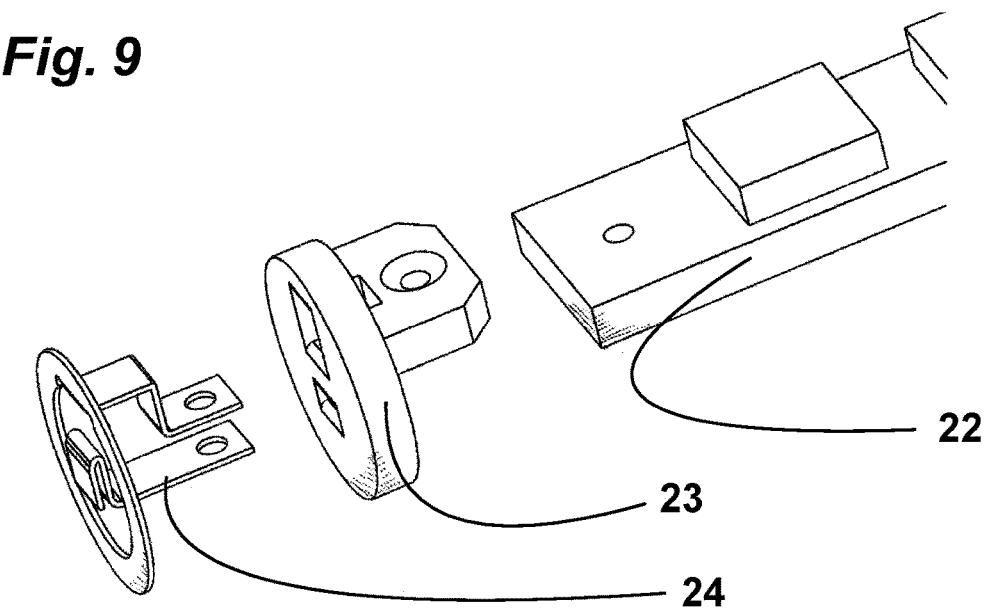
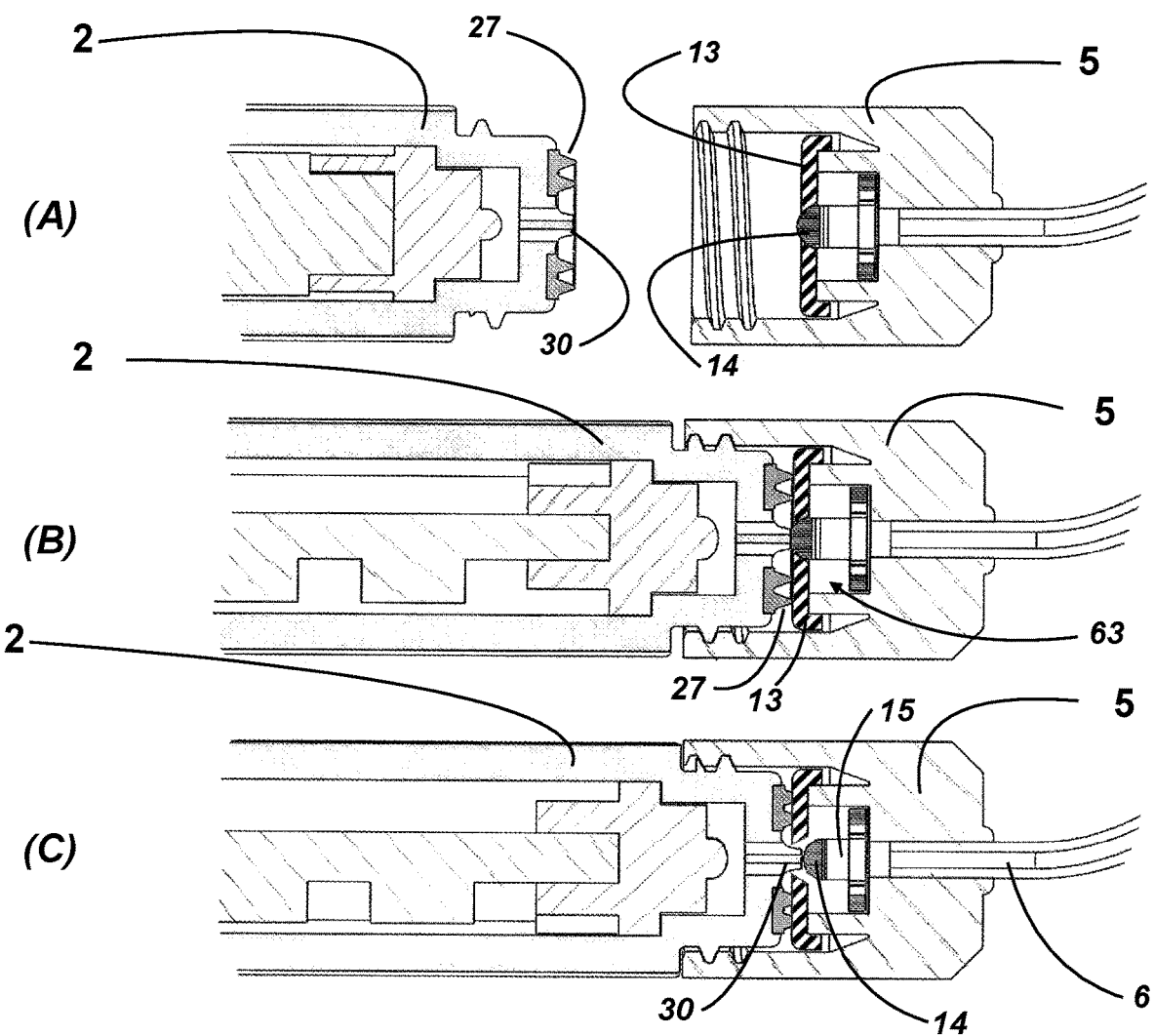
Fig. 10

DEVICE FOR THE DIRECT DETECTION OF THE ENDOVASCULAR PRESSURE OF A FLUID IN A VESSEL

The present invention relates to a device for the direct detection of the endovascular pressure of a fluid in a vessel, which can be used for example during the haemodyalisis treatments.

Generally, such detection device has a needle, constituting a vascular access to said fluid, and a duct which is in fluid communication with a distal end of the needle, as well as a disposable portion having a needle-holding element including said needle. Furthermore, the device comprises a pressure sensor.

Currently, the direct measurements of endovascular pressure, that is inside a blood vessel, take place by means of detection devices which are equipped with a vascular access, for example a needle terminal or other type of catheter with peripheral, cardiac or central access; these devices substantially belong to two categories, which distinguish one from the other one due to the position assumed by the pressure sensor: on the terminal lumen of the vascular access in a first case or outside thereof in a second case, however in any point connected to the vascular system downwards a duct connecting such point to the vascular access.

The devices belonging to the first one of said typologies are usually equipped with a miniaturized pressure sensor, suitable to be directly introduced into the blood vessel and electrically wired for the related power supply and transmission of the measurement signal towards outside. Then, they perform a direct measurement of the endovascular pressure.

US patent application No. 2010/0094143 A describes a cardiac catheter with a needle intended to be inserted for example in the pericardial space; on the distal end of the needle a pressure sensor is directly mounted to measure the pressure inside the lumen wherein the needle is inserted.

On the contrary, U.S. Pat. No. 5,954,701 B describes a cannula needle on the distal end thereof a device is inserted for the pressure measurement.

However, it is to be noted that in none of these examples the pressure of a blood flow, or a flow of a saline, dialytic, etc. solution flowing into the catheter is detected.

According to the second type, an auxiliary duct branches from the lumen of the vascular access in use, the duct being typically filled up with blood, saline solutions or another liquid, ending with an elastic membrane, the deformation thereof depending upon the pressure applied thereto.

This deformation is measured by means of a sensor, for example optical or of other type, and it allows an indirect detection of the pressure in the vessel wherein said vascular access insists. However, the indirect detection could not have the required accuracy, in particular as far as the measurement sensibility is concerned.

Examples of this second type are schematically described in U.S. Pat. No. 3,786,810 B, which however describes even a possible insertion of a sensor for the measurement of the pressure inside a cannula.

U.S. Pat. No. 7,927,270 B describes several examples of pressure sensors indirectly measuring the pressure inside a catheter or a needle of any nature, or even inside the beak of a syringe. Other examples are described in U.S. Pat. No. 3,807,389 B and in British patent application No. GB 2,488,810 A.

At last, U.S. Pat. No. 5,454,374 B describes a system for measuring the blood pressure in a haemodialysis device wherein the pressure is detected from the height of a blood column directly by a needle for tests.

In an additional type of devices for the direct detection of the endovascular pressure, the fluid inside the vessel is in contact with an air column, formed in a catheter or a capillary, and the pressure variations are detected on the air column.

An example of this type of device is described in International patent application No. WO 2014/054791, wherein the air column branches from a needle-holding element through a catheter connected directly to a pressure sensor, without any caution related to the possible pollution or infection in the air column which could be transmitted to the fluid.

The same serious problem is detected even in the device described in the European patent application N. 2,301,610 A2.

The critical aspects of the first type of devices to measure the pressure consist in the need for having to insert a sensor inside a vessel or an element which must have an inside volume sufficiently wide to receive it, and in that for the pressure detection usually a specific access is performed, then hardly usable for other medical purposes such as the infusion of therapeutic liquids or the extra-body circulation.

Furthermore, the need for using disposable devices makes necessary the removal of transducers and related wiring.

As far as the above-mentioned second type is instead concerned, it is noted that the indirect nature of detecting the endovascular pressure makes the measurement not sufficiently accurate, the measurement accuracy depending both from the membrane deformability which, among other things, has a linear elastic constant only if the shifting of the membrane centre does not exceed half thickness thereof, and for the presence of a transmission chain of the pressure wave constituted by the liquid inside the catheter which introduces a hydraulic resistance due to the viscosity thereof, as well as a hydraulic inertia due to the mass thereof.

Furthermore, considering the blood nature, the use of anticoagulant agents, such as heparin, can be used, to avoid the formation of coagula in blood which could invalidate the correct detection of the blood pressure.

An additional critical aspect, common to the above-illustrated solutions as determined by the structural features thereof, lies in the need for a wiring to connect the used sensors to outer devices for treating the signal and/or for the power supply of the transducers, which makes not possible to use them as medical devices which can be worn.

The technical problem underlying the present invention is to provide a device for the direct detection of the endovascular pressure allowing to obviate the drawbacks mentioned above with reference to the known art.

Such problem is solved by means of a device for the direct detection of the endovascular pressure as above specified and as defined in the enclosed claim 1.

The main advantage of the device for the direct detection of the endovascular pressure according to the present invention lies in the increase in the measurement accuracy, related to both static and dynamic quantities, detected through the air column which, inside said capillary ducts, is in contact with the endovascular fluid which exerts its pressure thereon, by separating at the same time such air column from outside in each process phase, and then by preventing that the fluid, the pressure thereof is to be measured, is polluted or infected thereby.

Differently from what noted in the devices belonging to the above-mentioned first category, now it becomes possible to perform measurements continuously on a flow of liquids from and towards a vessel, for example during treatments wherein an exchange of fluids through the same vessel takes place, as it happens in haemodialysis.

Moreover, the measurement is possible even in absence of liquids inside the duct for transmitting the pressure wave, which makes unnecessary the use of anticoagulants.

At last, the separation between the portion for acquiring the treatment and transmitting the signal with respect to the portion referred to the access to the vessel is implemented, by allowing to make the latter disposable.

In fact, according to preferred examples of the device according to the present invention, they are substantially constituted by two portions: the first one is a disposable portion; it includes a needle, equipped with a coaxial cannula with suitable geometry, which forms a capillary duct hydraulically connected, through a flexible duct, to a connector suitable to the connection to a second portion which is a re-usable portion and which comprises the transducers, the electronics for managing and controlling the related signals, a radiofrequency transmission module and a battery electric source. Said re-usable portion is mainly an element with small sizes which often constitutes the handle of the device and which is suitable to be placed and/or fastened to any portion of the patient's body, for example by means of an adhesive patch.

In particular, the connector, which is present in the first disposable portion, comprises a valve which is usually closed, but made permeable to the passage of fluids only upon the moment of connecting, for example by screwing, to the mentioned second portion.

In this way, upon inserting the needle in the vessel, the air column included in the connection line between the capillary duct and the connector itself is not dispersed towards the environment and it remains compressed inside the same line.

Such effect is determined only by the fact that the diastolic and systolic pressures, in each case, are higher than the environmental ones, then the lumen of the needle, seat for detecting the endovascular pressure, moves, upon the insertion in the vessel, from a lower pressure to a growing pressure.

Subsequently, the connector and the re-usable portion are connected, through two distinct phases, to a suitably shaped seal which will put in hydraulic continuity the terminal portions of the connector and of the re-usable portion whereas, in the second phase, the opening of the valve present on the connector will take place by means of a suitable mechanical actuation. This makes that the small volume inside the re-usable portion, which includes the sensors and which is hermetically closed, is placed in connection to the air column present in the disposable portion without substantially altering the volume content thereof and without putting it in communication to the outer environment, thus by keeping the same level of inside pressure.

Then, in close proximity to the lumen of the needle a separation surface between blood and air will form which will oscillate around an equilibrium position only due to the effect of the pressure variations localized therein, the elastic wave thereof is transmitted in the air present inside the line towards the sensors present on the handle for a direct and continuous measurement.

The present invention will be described hereinafter according to a preferred embodiment thereof, provided by way of example and not with limitative purposes, by referring to the enclosed drawings wherein:

FIG. 3 shows a cross section of a detail of the device of FIG. 1;

FIG. 4 shows an enlarged partial view and in longitudinal section of the device of FIG. 1, in particular of the disposable portion;

FIG. 9 shows an exploded partial view of a detail of the re-usable portion of FIG. 7; and FIG. 10 shows a sequence A-B-C of views in longitudinal section of the device of FIG. 1, which illustrates three respective connection phases of the disposable portions and which can be re-used, of the previous figures.

Referring to the figures, a device for the direct detection of the endovascular pressure is designated as a whole with 1. The embodiment which will be described hereinafter has the shape of a catheterisation with a butterfly needle.

Figure 1:
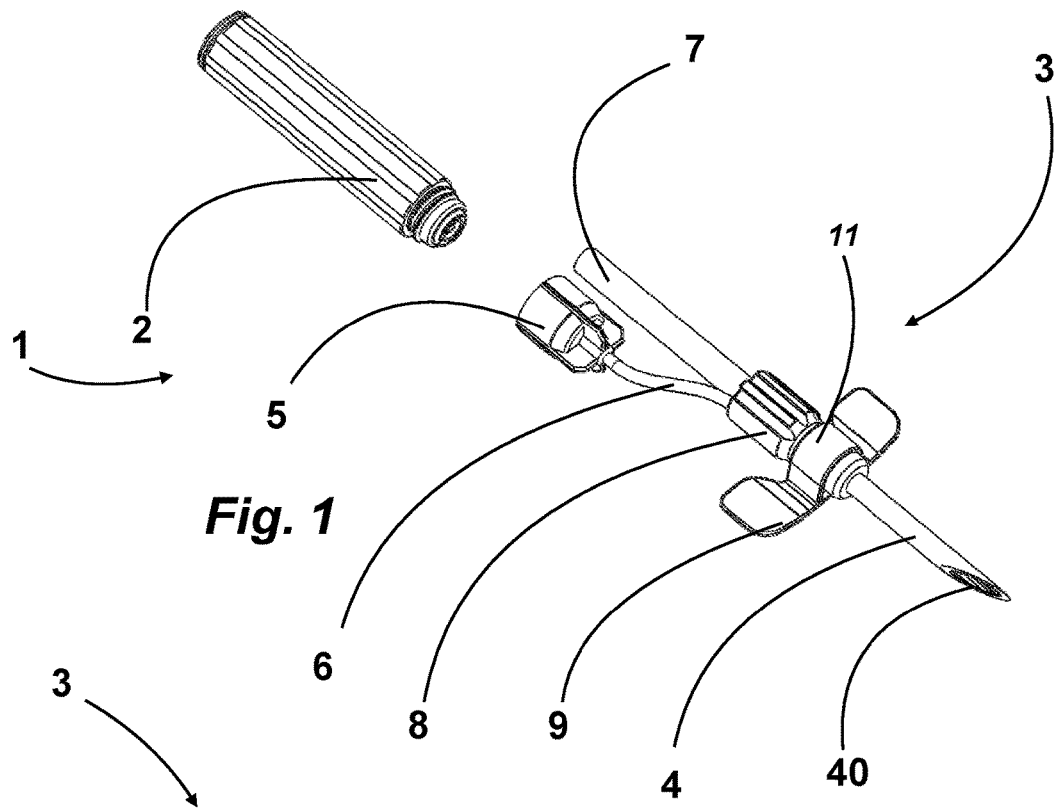
FIG. 1 shows an axonometric view of an embodiment of device for the direct detection of the endovascular pressure according to the present invention.
Figure 2:
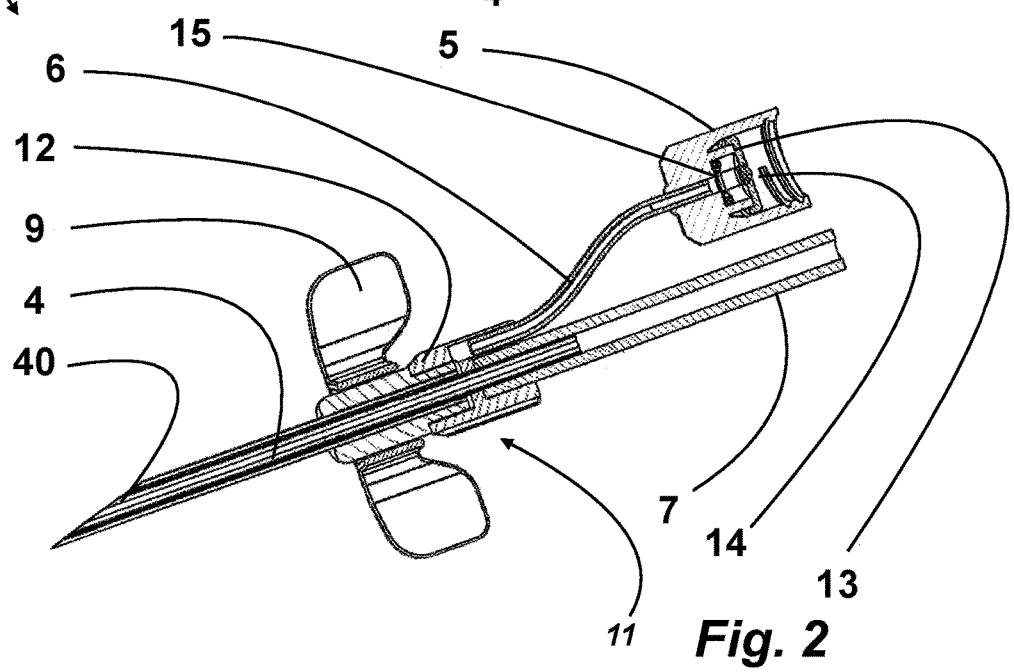
FIG. 2 shows an axonometric view in longitudinal section of a disposable portion of the device of FIG. 1.

It is constituted (FIG. 1) by a reusable portion 2 which has the shape of a substantially cylindrical handle, with longitudinal ribs, which will be described hereinafter with greater detail, and by a disposable portion 3 comprising, in turn, a hollow metallic needle 4 with an open tip 40, intended to be inserted in a site of the patient's body.

The needle 4, typically made of metallic material, has a distal end 41 coupling to the proximal end of a catheter 7 (FIG. 4), coaxial to the needle 4, and it further includes a cannula 10 implementing a fluid line therewith with the hydraulic continuity for the passage and/or collection of a physiologic liquid. To this purpose, the cannula 10 extends in the catheter 7 at the proximal end thereof 44.

The catheter 7, conventionally implemented by a flexible duct, thus constitutes a fluid-connecting line which is only partially represented in the figures, which is suitable to be connected for the interconnection to other therapeutic or diagnostic devices, in particular but not exclusively medical machines for injecting or draining fluids from the human body, such as for example it happens in treatments with extrabody circulation.

At the connection between the needle 4 and the catheter 7, the device 1 comprises a tubular support 8, in the shape of one of a pair of bushings arranged on the same axis, to form a common passage channel crossed by the needle 4 and by the duct 7. The support 8 can be made of plastic material.

The tubular support 8 is substantially constituted by two portions: the first one thereof is a first cylindrical element which constitutes a needle-holding element 11 of the disposable portion 3, which is crossed by the needle 4, comprising a pair of small wings 9 with a typical butterfly-like configuration. It has a shank 42 whereon a second cylindrical element is inserted which constitutes the catheter-holding element 80, having a coupling with a forced or glued interlocking inside a proximal joint 12 of said catheter-holding element 80.

The small wings 9 allow to fasten the needle-holding element 11 to the patient by means of patches or other adhesives by allowing at the same time the rotation of the support 8 of the needle 4 should it be necessary to adjust the position of the needle inside the blood vessel.

The catheter-holding element 80 also comprises a distal joint 43 opposite to the proximal joint 12. The proximal end 44 of the catheter 7 is inserted inside the distal joint 43, by means of a forced or glued interlocking.

The needle 4 and the catheter 7 are crossed inside by a cannula 10 which has a proximal end arranged at the tip 40 of the needle: in this way, it is wetted by the body fluid upon inserting the needle 4 in the target site thereof. The cannula 10 extends from the tip 40 of the needle as far as the proximal end 44 of the catheter 7.

Considering that the duct inside the needle 4 is cylindrical with a circular section, the cross section of the cannula 10 provides a plurality of points 45 in contact with the inner surface of the cavity of the needle 4 connected by thin walls 46 which form, between them and the inner surface of the cavity of the needle 4, a corresponding plurality of capillary ducts 16.

It is to be meant that the cannula 10, coaxial to the needle 4, can be implemented with several different geometries, even in relation to the shape of the section of the needle 4, which could be not circular but, for example, oval, and in this case the cannula could have a circular section. Generally, the section of the cannula 10 is shaped so as to form one or more capillary ducts 16 with the inner surface of the needle, branching from the lumen of the needle 4 towards an intermediate catheter 17 which has an interstitial volume arranged inside the tubular support 8, in particular the second cylindrical element 80, joining the needle 4 to the catheter 7, at the terminal edge of the shank 42 of the place inside the support 8 between the needle holder 11 and the flange 12.

At the distal end of the needle 41, the cannula 10, extending inside the catheter 7, forms outside a sealing 47 at the distal joint 43.

Therefore, the inside of the needle 4 is put in fluid connection with the catheter 7 through the inner section of the cannula 10, whereas the capillary ducts 16 are connected to said intermediate cavity 17 inside the tubular support 8. It extends radially between the needle-holding element 11 and the catheter-holding element 80 so as to communicate with a door 48 which longitudinally extends as far as the distal end 49 of the catheter-holding element 8 and the tubular support 8.

The proximal end 61 of an auxiliary duct 6 is inserted inside the opening 48, the duct extending outside the tubular support, from the needle-holding element 11 as far as a connector 5 which is useful to connect the above-described disposable portion 3 to the above-mentioned reusable portion 2.

The auxiliary duct 6 is formed by a flexible catheter, similar to the main catheter 7.

Figure 5:
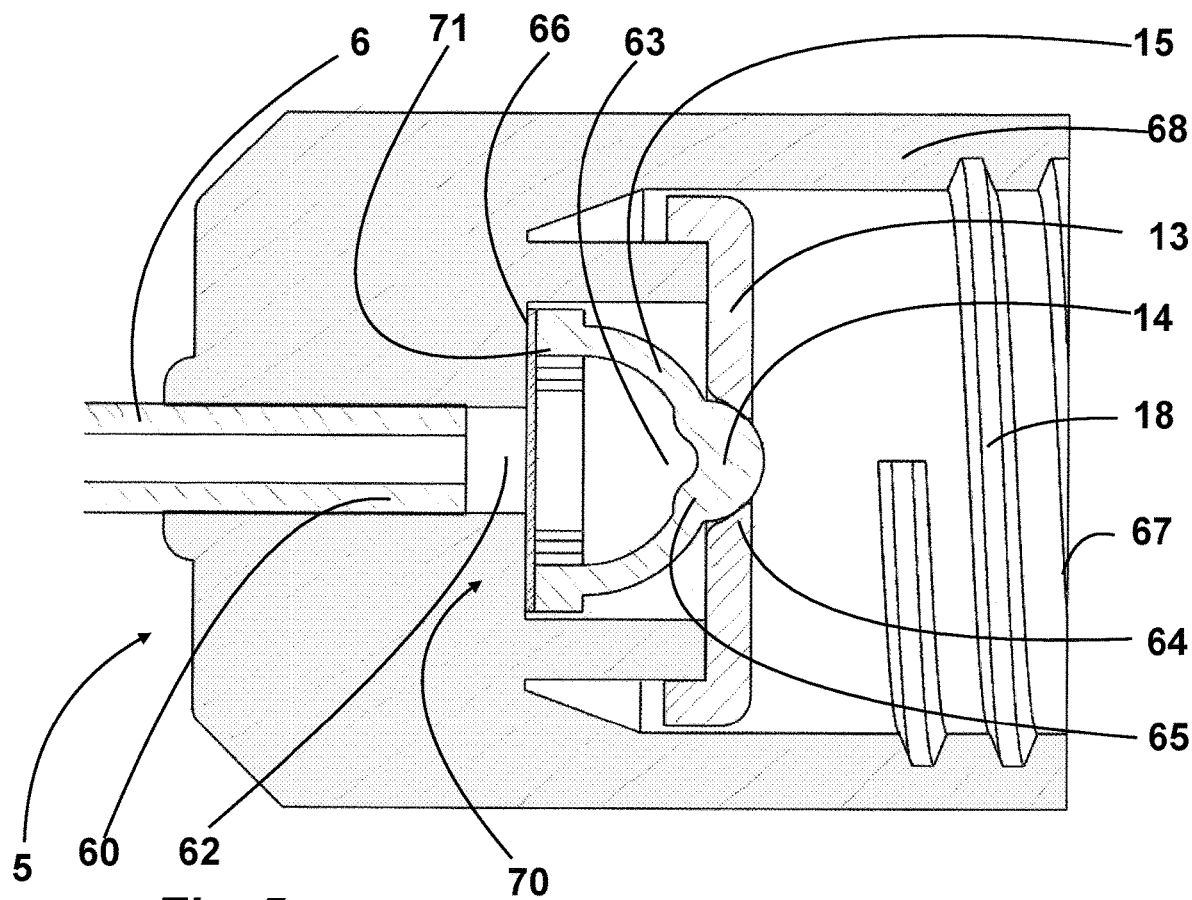
FIG. 5 shows an enlarged partial view in longitudinal section of another detail of the device of FIG. 1.

The distal end 60 of the auxiliary duct 6 is fastened to the connector 5 inside a suitable cylindrical hole thereof 62 (FIG. 5) by means of forced and/or glued interlocking, thereat a terminal cylindrical cavity 63 is formed which has a larger diameter than the inner diameter of the auxiliary duct 6.

The terminal cavity 63 has a pierced cover 13, which closes it inside the connector 5, and also includes a membrane 66 and a valve element 70.

Said valve element 70 is formed at the base thereof by an annular base 71 therefrom an elastic arc 15 branches, at the top thereof there is a spherical projection which has the function of shutter 14. The cover 13, fixed to the connector 5 for example by welding, in central position has a conical hole 64 which constitutes a valve opening suitable to receive the shutter 14 with a sealed complementary coupling. It is to be noted that said shutter 14, connected to the elastic arc by means of a joint 65, substantially is part of the elastic arc 15.

During the assembling, the membrane 66 and the annular base 71 of the valve element 70 result to be compressed by contrast between the cover 13 and the bottom of the intermediate cavity 63 existing in the connector 5.

In this configuration, the forced contact between the shutter 14 and the conical hole 64 on the cover 13 generates a hydraulic sealing which, by acting as a closed valve, insulates the flexible duct 6 from the environment.

Furthermore, the membrane 66 separates the hole 62 which receives the distal end of the auxiliary duct 6 and the terminal cavity 63 inside the connector 5.

Then, the membrane 66, thanks to the selective porosity thereof, acts as anti-contamination barrier towards the inside of the flexible duct 6 as it is of a type commonly used in the medical field, that is permeable to air but not to bacteria or other pathogens.

The connector 5 further has a connecting opening 67, opposite to the hole 62 which receives the distal end of the auxiliary duct 6, open on said cover 13 and on the elastic projection 14 projecting from the through opening and formed by cylindrical walls 68 inside thereof a nut 18 is formed suitable to receive a corresponding screw profile placed at a connection end of the re-usable portion 2 of the device 1.

Figure 6:
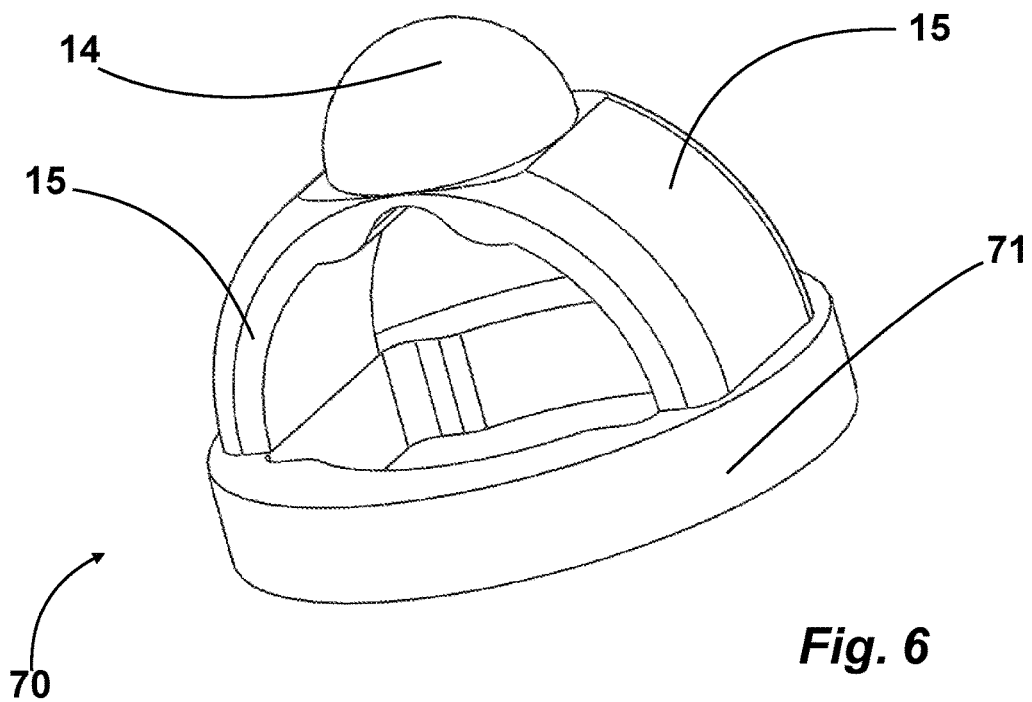
FIG. 6 shows an axonometric view of a component of the device of FIG. 1.

The reusable portion 2, as it can be seen in the exploded view of FIG. 6, is constituted by a tubular casing 19 extending between a proximal detection end 73 and a distal access end 74; internally it receives a group 20 formed by an electronic card 22, and it is closed on the closing end 74 by a closing stopper 28.

Figure 7:
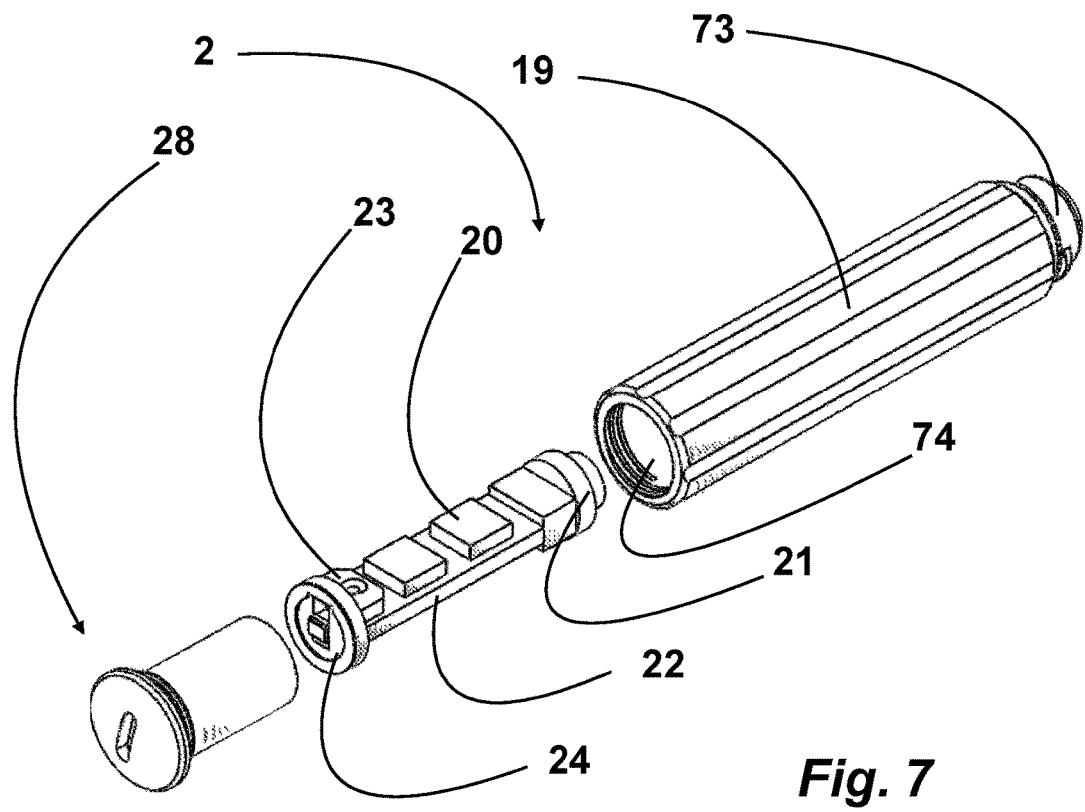
FIG. 7 shows an exploded axonometric view related to a re-usable portion of the device of FIG. 1.
Figure 8:
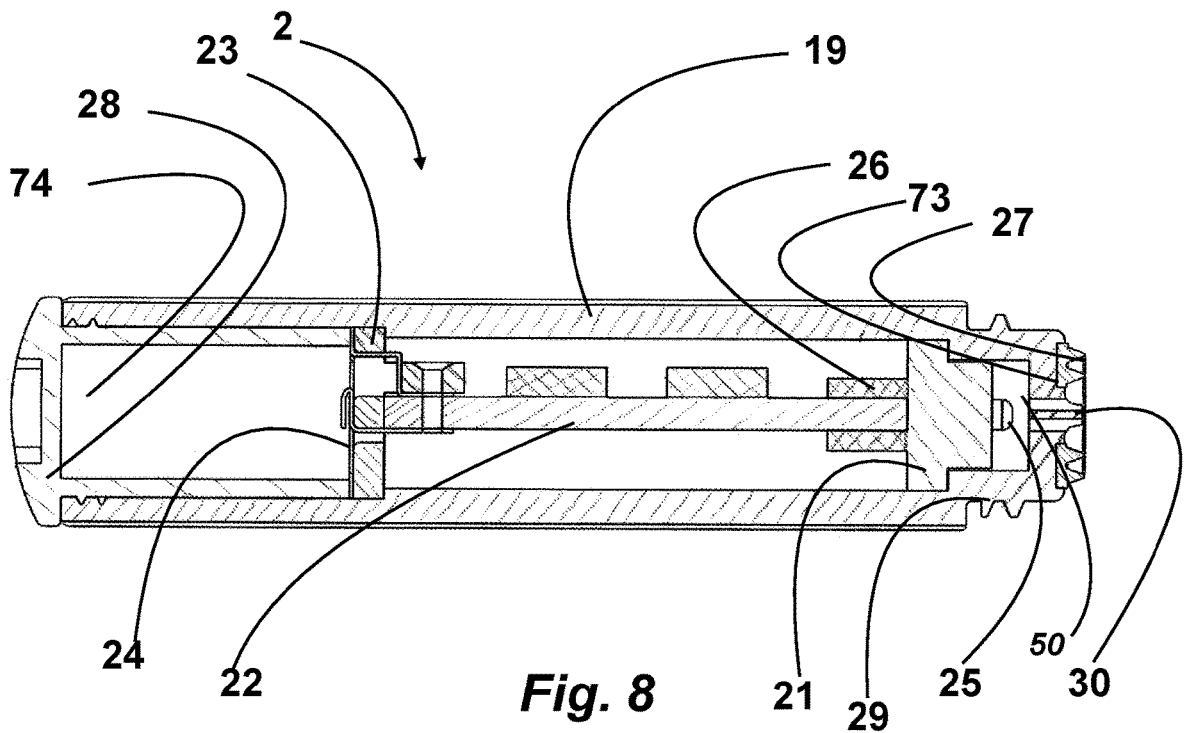
FIG. 8 shows a view in longitudinal section of the re-usable portion of FIG. 7.

In particular, the group 20, in turn, is formed by an electronic card 22 and by a pick-up 21 made of plastic material bearing at the ends thereof one or more pressure sensors 25 (FIG. 7) and an electric connector 26 for the coupling connection with the electronic card 22, respectively. The sensor 25 is arranged in a suitable inner space 50 of the re-usable element 2, apt to be faced towards the connector 5 of the disposable element 3.

Moreover, the pick-up 21 couples by mechanical interference to the outer casing 19 by generating a sealing and forming inside the volume wherein the pressure measurement takes place.

The electronic card 22 then implements the function of receiving the signal of sensors, the related treatment by means of microprocessor and the radiofrequency transmission towards an outer receiving device.

The group 20 on the end of the card 22 opposite to the pick-up 21 further includes a ferrule 23 which allows to house conducting elements 24 made of conductive plate which, fastened with a screw and a plastic bolt to the card 22, allow the power supply of the same.

The ferrule 23 constitutes the bottom plate of a compartment for housing a battery, not represented in figures, inside the stopper 28, made of conductive material, which also has the function of closing the casing 19 sealingly, by screwing 19; this configuration puts in electric continuity the battery poles and the electronic card 22 through the above-mentioned metal plates 24.

At the detection end 73, the reusable element 2, in proximity of the sensor 25, there is a leading seal 27 with toroidal shape made of medium-hard elastomer, which surrounds said inner space 50. Such end 71 has a screw profile 29 complementary to the above-mentioned nut 18 of the connector 5.

At last, such end has a projection 30 projecting in the centre of the proximal end 73 and which, as it will appear hereinafter, is intended to interfere with the shutter 14 of the valve element 70, to cause the opening of the valve associated thereto. The projection 30 further comprises one or more axial through holes, intended to put into communication the terminal cavity 63 of the connector 5 with the inner space 50 which receives the pressure sensor 25.

The proximal end 73 of the casing 19, that is of the reusable element, and the opening 67 of the connector 5 constitute means for connecting the reusable element with the disposable element 3, thereto the connector 5 belongs, which activates the valve, implemented by the shutter 14 of the valve element 65, and by the cover 13 with its through opening which puts into communication the pressure sensor 25 and the cavity 63 wherein a separation of its inner volume is implemented by means of the membrane 66 with selective porosity, so as to allow the air passage and to constitute a barrier for contaminating agents.

It is to be meant that, in alternative versions, said membrane could be arranged directly on the support including the above-mentioned needle-holding element, without the need for arranging the auxiliary duct which separates said support from the connector, which on the contrary could be integrated therein.

Furthermore, the valve could assume other shapes, activated upon connecting the reusable portion with the disposable portion.

The use of the device described so far is outlined hereinafter. Firstly, the needle 4 is inserted inside a body vessel. This can take place for example in a haemodialysis treatment, but in each case the inner cavity of the needle 4, therefrom the capillary ducts 16 branch, is put in contact with the blood bolus thereof one wants to know the pressure. Since said capillary ducts 16 are in fluid connection with the volume of the terminal cavity 63 inside the connector 5, which in this first phase A (FIG. 9) is closed by the valve formed by the elastic protrusion 14 and by the covers 13, therealong, in proximity of the cavity of the needle 4, separation surfaces between blood and air will form which will oscillate around an equilibrium position due to the effect of the pressure action inside the vessel e the elastic reaction of the air column included inside the line formed by the capillary ducts 16, the interstitial volume 17, the auxiliary duct 6 and the above-mentioned volume inside the connector 5.

It is to be noted that said air column will result in overpressure with respect to the outer environment, proportionally to the values of the systolic and diastolic pressures which are characteristic of the blood vessels.

Then, in a second phase B, the reusable element 2 is screwed to the connector 5 by inserting the leading sealing 27 in the connector 5 by sealing the volume inside the connection opening.

Subsequently, by continuing the screwing procedure in a third phase C, the extruded profile 30 is inserted inside the opening 64 of the cover 13, by pushing the projection 14 towards the internal portion of the cavity 63, by putting in fluid communication the volume inside the reusable element, with the pressure sensor 25, with the volume of the inner cavity 63 of the connector 5 and, through the membrane 66, with the inner cavity of the needle 4.

This last procedure takes place in insulation from the outer environment and makes that there are neither a perturbation of the pressure in the air column inside the device nor a substantial variation in the position of said separation surfaces between blood and air, which remain confined inside the needle 4.

Then, in its final configuration, the device allows to connect, through an elastic fluid such as air, the tip 40 of the needle 4 and the pressure sensors 25 placed in the re-usable element 2, thus allowing an accurate and continuous detection of the endovascular pressure.

To the above-described device for the direct detection of the endovascular pressure a person skilled in the art, in order to satisfy additional and contingent needs, could bring additional modifications and variants, all however comprised within the protection scope of the present invention, as defined by the enclosed claims.

The invention claimed is:

1. A device (1), for direct detection of endovascular pressure of a fluid in a vessel, which has a disposable portion (3) comprising:
   a needle-holding element (11) including a needle (4), with an open tip and inner duct, constituting a vascular access to said fluid;
   one or more capillary ducts (16) arranged in the inner duct and configured to be passed through by said fluid when the needle is being used;
   a connector (5), comprising a valve (13, 14), defining a connecting terminal cavity (63) which is arranged outside said needle-holding element (11) and is in fluid communication with said one or more capillary ducts (16) through a duct (6) extending from said needle-holding element (11) to said connector (5), wherein said connector (5) comprises a membrane (66) with selective porosity, so as to allow passage of air and to constitute a barrier for contaminating agents, which separates said valve (13, 14) from said duct (6); and
   a re-usable element (2) including at least a pressure sensor (25) and comprising means for connecting to said connector (5) at said terminal cavity (63) of the disposable portion (3), apt to put into communication an inner space (50) of said re-usable element (2), which receives said at least a pressure sensor (25), with said terminal cavity (63),
   the opening of said valve (13, 14) being determined by the connection between the re-usable element (2) and said disposable portion (3) so that, in a first phase wherein said valve (13, 14) is closed, in said one or more capillary ducts (16) respective separation surfaces between said fluid and air are formed, oscillating around an equilibrium position due to an effect of the action of the pressure inside the vessel and of an elastic reaction of the air column included between such separation surfaces and the valve (13, 14), in overpressure with respect to the outer environment, and so that, in a subsequent phase wherein the connection between the re-usable element (2) and said disposable portion (3) determines the opening of said valve (13, 14), said air column is in communication with the inner space of said re-usable element (2).

2. The device (1) for the direct detection of the endovascular pressure according to claim 1, wherein said one or more capillary ducts (16) are formed by a cannula (10) inserted inside the needle (4), between the walls (46) of the cannula (10) and the inner surface of the needle (4), the cannula (10) being arranged for the passage of the endovascular fluid and having a proximal end near the tip (40) of the needle (4).

3. The device (1) for the direct detection of the endovascular pressure according to claim 2, wherein a distal end (41) of the needle (4) is connected to a catheter (7), the cannula (10) extending in said catheter (7) in a proximal end thereof (44) by forming a sealing (47) therewith to insulate the catheter (7) from said one or more capillary ducts (16).

4. The device (1) for the direct detection of the endovascular pressure according to claim 3, wherein the needle-holding element (11) includes an intermediate catheter (17) which has a volume arranged in fluid communication with said one or more capillary ducts (16), at the distal end (41) of the needle (40), and with said duct (6) connecting the intermediate cavity (41) to said connector (5) of the disposable element (3).

5. The device (1) for the direct detection of the endovascular pressure according to claim 4, wherein said duct (6) is a flexible catheter.

6. The device (1) for the direct detection of the endovascular pressure according to claim 2, wherein the cannula (10) has a section which is shaped so as to form one or more capillary ducts (16) with the inner surface of the needle (4), said cross section having points (45) in contact with the inner surface of the needle (4).

7. The device (1) for the direct detection of the endovascular pressure according to claim 1, wherein said valve in said connector (5) has:
 a pierced cover (13), so as to obstruct internally said terminal cavity (63), which comprises a through opening (64); and
 a valve element (70) which comprises an elastic support (15) and a shutter (14), formed in the elastic support (15), apt to sealingly couple with said through opening (64).

8. The device (1) for the direct detection of the endovascular pressure according to claim 7, wherein said valve element (70) comprises an annular base (71) and wherein said elastic support (15) has an arc-like shape, which deforms when said shutter (14) is pressed outside by said pierced cover (13).

9. The device (1) for the direct detection of the endovascular pressure according to claim 8, wherein said elastic element is comprised between said membrane (66) and said pierced cover (13).

10. The device (1) for the direct detection of the endovascular pressure according to claim 8, wherein the connector (5) has a connecting opening (67) apt to receive a connection end of the re-usable portion (2) of the device (1) which comprises a projection (30) which, once the insertion is performed, presses on said shutter (14) through the valve opening (64) formed in said pierced cover (13), by determining the opening of the valve (13, 14).

11. The device (1) for the direct detection of the endovascular pressure according to claim 1, wherein said re-usable element (5) comprises a leading seal (27) which, in an intermediate phase preceding the opening of the valve (13, 14) during the connection between connector (5) and re-usable element (3) insulates said terminal cavity (63).

* * * * *